(12) United States Patent
Fojtik

(10) Patent No.: US 9,022,971 B2
(45) Date of Patent: *May 5, 2015

(54) DOUBLE BARREL SYRINGE AND HANDLES FOR USE WITH DOUBLE BARREL SYRINGES

(71) Applicant: Shawn P. Fojtik, Park City, UT (US)

(72) Inventor: Shawn P. Fojtik, Park City, UT (US)

(73) Assignee: Control Medical Technology, LLC, Park City, UT (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/725,433

(22) Filed: Dec. 21, 2012

(65) Prior Publication Data

US 2013/0110036 A1 May 2, 2013

Related U.S. Application Data

(63) Continuation of application No. 12/649,190, filed on Dec. 29, 2009, now Pat. No. 8,337,450, which is a continuation of application No. 11/877,529, filed on Oct. 23, 2007, now Pat. No. 7,674,247.

(60) Provisional application No. 60/853,878, filed on Oct. 24, 2006.

(51) Int. Cl.
| | |
|---|---|
| *A61M 5/178* | (2006.01) |
| *A61M 3/02* | (2006.01) |
| *A61M 5/19* | (2006.01) |
| *A61M 5/145* | (2006.01) |
| *A61M 5/315* | (2006.01) |
| *A61M 5/31* | (2006.01) |

(52) U.S. Cl.
CPC ........... *A61M 3/0233* (2013.01); *A61M 5/1456* (2013.01); *A61M 5/1782* (2013.01); *A61M 5/19* (2013.01); *A61M 5/31511* (2013.01); *A61M 2005/3139* (2013.01); *A61M 2205/05* (2013.01)

(58) Field of Classification Search
CPC .......... A61M 5/31511; A61M 1/0009; A61M 1/0058
USPC ............. 604/36, 38, 181, 187, 191, 233, 234, 604/235
See application file for complete search history.

(56) References Cited

U.S. PATENT DOCUMENTS

| | | | |
|---|---|---|---|
| 5,957,883 A | 9/1999 | Lin | |
| 6,245,046 B1 | 6/2001 | Sibbitt | |
| 6,585,696 B2 | 7/2003 | Petersen et al. | |
| 6,827,701 B2 | 12/2004 | MacMahon et al. | |
| 7,041,084 B2 | 5/2006 | Fojtik | |
| 7,534,234 B2 | 5/2009 | Fojtik | |
| 7,674,247 B2 * | 3/2010 | Fojtik | ............................ 604/191 |

(Continued)

*Primary Examiner* — Aarti B Berdichevsky
(74) *Attorney, Agent, or Firm* — Durham Jones & Pinegar, P.C.

(57) ABSTRACT

An apparatus that includes two syringes, or a "double barrel syringe," includes one syringe that injects or infuses while the other syringe aspirates. In the double barrel syringe, injection and aspiration may be effected by a single action. The double barrel syringe may include a handle with two members. A first member of such a handle includes one arm that pivotally couples to a plunger of a first syringe and another arm that pivotally couples to a barrel of a second syringe. A second member of the handle includes one arm that pivotally couples to a barrel of the first syringe and another arm that pivotally couples to a plunger of the second syringe. Methods for injecting or infusing simultaneously with aspirating are also disclosed.

14 Claims, 7 Drawing Sheets

(56) References Cited

U.S. PATENT DOCUMENTS 8,337,450 B2 * 12/2012 Fojtik .............................. 604/36
2006/0270996 A1    11/2006 Fojtik
2008/0154209 A1 *   6/2008 Fojtik ............................ 604/191
2010/0100033 A1 *   4/2010 Fojtik .............................. 604/28

* cited by examiner

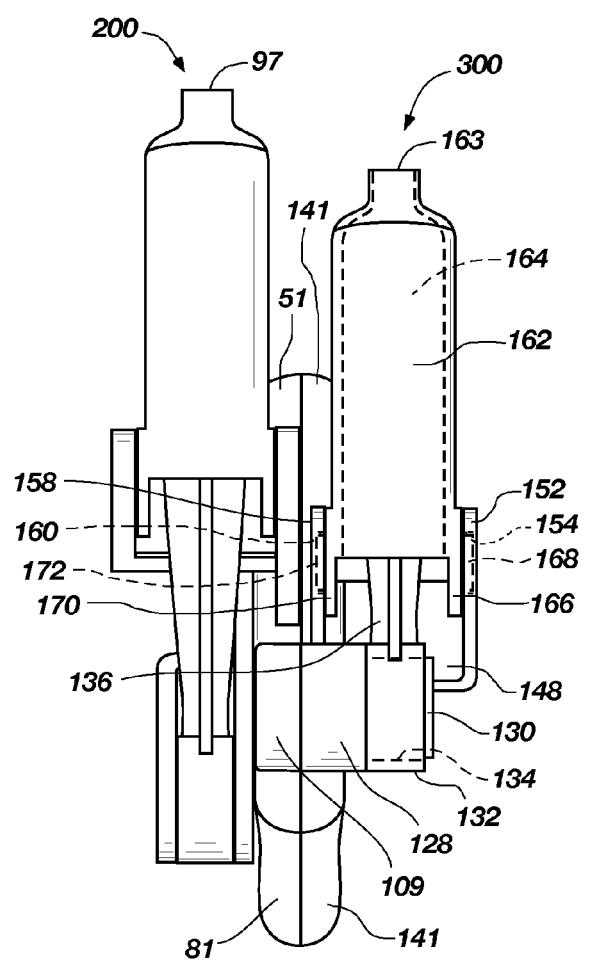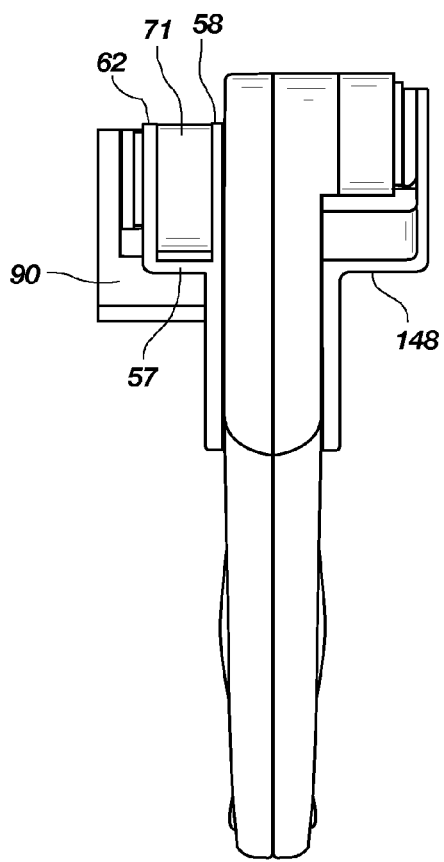
FIG. 11　　　　FIG. 12

DOUBLE BARREL SYRINGE AND HANDLES FOR USE WITH DOUBLE BARREL SYRINGES

CROSS-REFERENCE TO RELATED APPLICATIONS

This application is a continuation of U.S. patent application Ser. No. 12/649,190, filed Dec. 29, 2009, titled DOUBLE BARREL SYRINGE AND HANDLES FOR USE WITH DOUBLE BARREL SYRINGES, issued as U.S. Pat. No. 8,337,450, on Dec. 25, 2012, which was a continuation of U.S. patent application Ser. No. 11/877,529, filed Oct. 23, 2007, titled DOUBLE BARREL SYRINGE AND HANDLES FOR USE WITH DOUBLE BARREL SYRINGES, issued as U.S. Pat. No. 7,674,247, on Mar. 9, 2010, which claims the benefit of priority under 35 U.S.C. §119(e) to U.S. Provisional Application No. 60/853,878, filed Oct. 24, 2006, titled DOUBLE BARREL, INFUSION/ASPIRATION SYRINGE. The entire disclosure of each of the foregoing applications is hereby incorporated herein.

TECHNICAL FIELD

The present invention relates to apparatus that include two syringes, or to "double barrel syringes," with one syringe that injects or infuses while the other syringe aspirates. In particular, the present invention relates to hand-held, hand-operated double barrel syringes in which injection and aspiration may be effected by a single action. More particularly, double barrel syringes that incorporate teachings of the present invention include handles that resemble pliers to provide a mechanical advantage as fluids are simultaneously injected and aspirated by the barrels and their cooperating plungers.

SUMMARY

The present invention includes an apparatus with two syringes. Barrels of the two syringes are positioned adjacent to one another. Two plungers are disposed in or otherwise associated with the two barrels. Such apparatus are referred to herein as "double barrel syringes" or, more simply, as "syringes."

Both barrels and plungers of a syringe according to the present invention are associated with a single handle. The handle may comprise a plier-grip handle. Without limiting the scope of the present invention, the handle may include two members that include features that are associated with a first of the two syringes in the manner described in U.S. Pat. No. 7,041,084 or the manner described in U.S. application Ser. No. 11/431,377, filed May 9, 2006, the disclosures of both of which are hereby incorporated herein, in their entireties, by this reference. The members of the handle may also include features that are associated with a second of the two barrels in the manner described in U.S. Pat. No. 7,534,234, the disclosure of which is hereby incorporated herein, in its entirety, by this reference. The handles and syringes are arranged in a manner that facilitates concurrent movement of the plungers in opposite directions.

For example, when members of the handle are moved toward one another, the first plunger may be forced into its corresponding barrel (e.g., injection or infusion), while the second plunger may be drawn out of its corresponding barrel (e.g., aspiration).

Additional aspects, features, and advantages of the present invention will become apparent to those of ordinary skill in the art through consideration of the ensuing description, the accompanying drawings, and the appended claims.

BRIEF DESCRIPTION OF THE DRAWINGS

In the drawings, which depict features of various aspects of the present invention:

FIG. 5 is a view of the left side of the syringe;
FIG. 6 shows the right side of the syringe;
FIG. 7 depicts the top of the syringe; and
FIG. 8 illustrates the back of the syringe;

FIGS. 9 through 12 depict the embodiment of syringe shown in FIGS. 1 through 8 with the handles in an open orientation:

FIG. 9 shows the left side of the syringe;
FIG. 10 illustrates the right side of the syringe;
FIG. 11 depicts the top of the syringe; and
FIG. 12 is a view of the back of the syringe.

DETAILED DESCRIPTION

Figure 2:
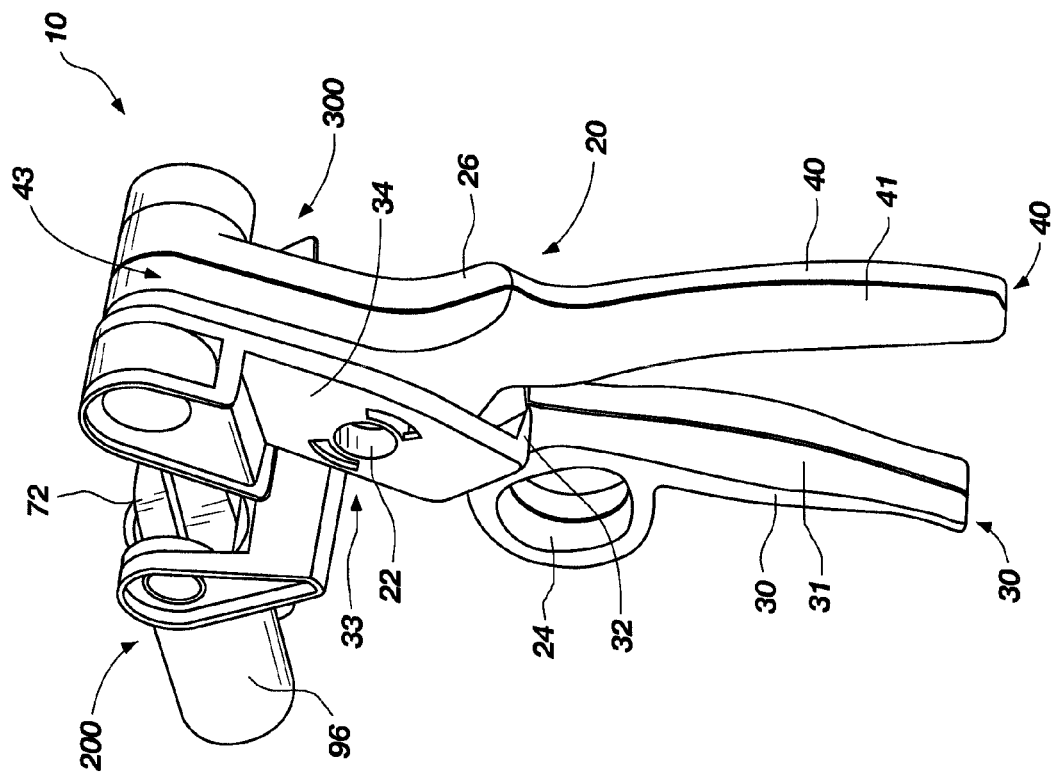
FIG. 2 is a rear perspective view of the embodiment of syringe shown in FIG. 1.
Figure 1:
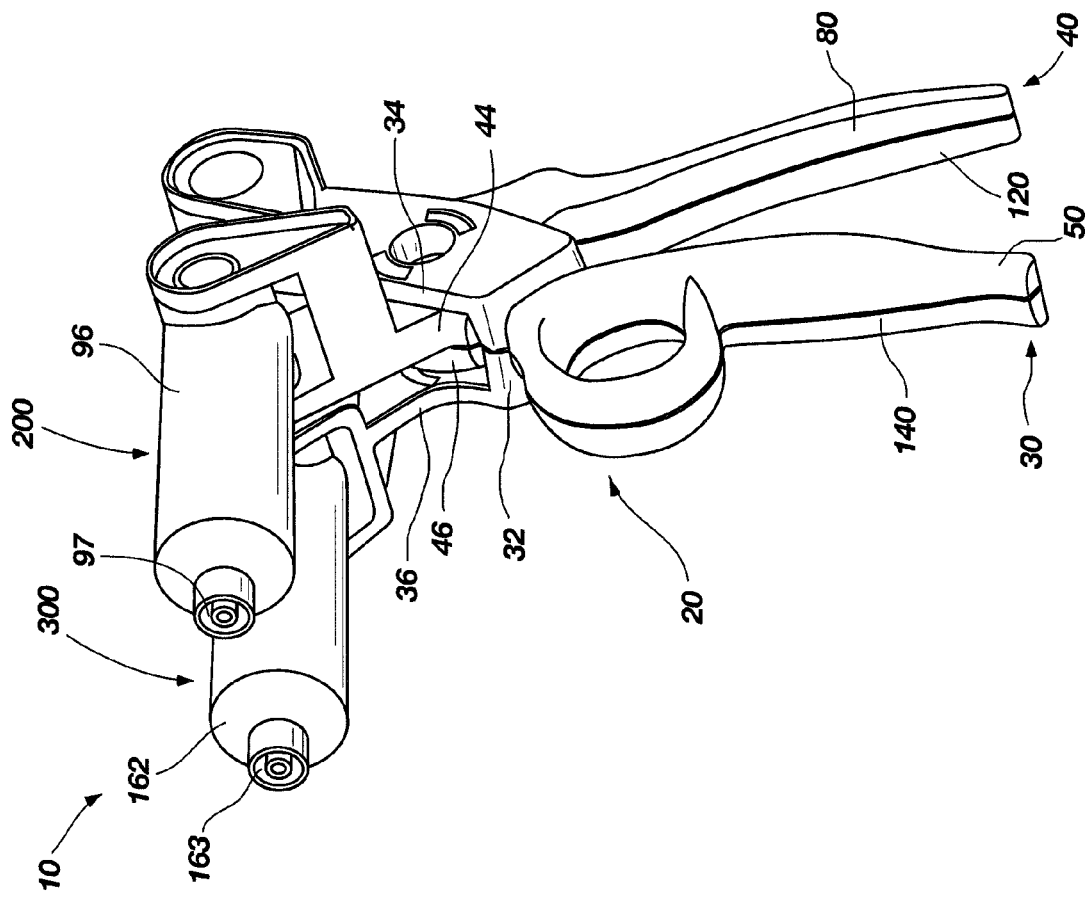
FIG. 1 is a frontal perspective view of an embodiment of a syringe that includes two barrels according to the present invention, showing handle members of the syringe in an intermediate position, in which distal ends of plungers are located in somewhat central regions of both barrels.

With reference to FIGS. 1 and 2 of the drawings, an embodiment of a syringe 10 that includes an infusion syringe 200 and an aspiration syringe 300 is shown. Infusion syringe 200 and aspiration syringe 300 are positioned side-by-side, with their distal ends 97 and 163 oriented in substantially the same direction.

A single pair of handles 20 is associated with, and simultaneously operates, infusion syringe 200 and aspiration syringe 300. The pair of handles 20 includes a first, front member 30 and a second, rear member 40. Front member 30 includes a proximal portion 31 with a surface that is configured to be grasped by the fingers of one of a user's hands, and may optionally include a ring 24 located and configured to receive the user's index finger. A proximal portion 41 of rear member 40 is configured to be grasped by the thumb and palm of the same hand, and may optionally include a retention feature 26 for receiving the thumb on that hand.

Front member 30 and rear member 40 are pivotally connected to one another by way of a hinge 22, which is positioned at locations along the lengths of front member 30 and rear member 40 that will provide optimal leverage when the pair of handles 20 is used. Without limiting the scope of the present invention, the location of hinge 22 may resemble the location of a hinge on pliers, with the lengths of distal portions 33 and 43 of front member 30 and rear member 40, respectively, being relatively short compared to (e.g., about half the lengths of) the lengths of proximal portions 31 and 41. Such an arrangement provides a user with a mechanical advantage.

Figure 3:
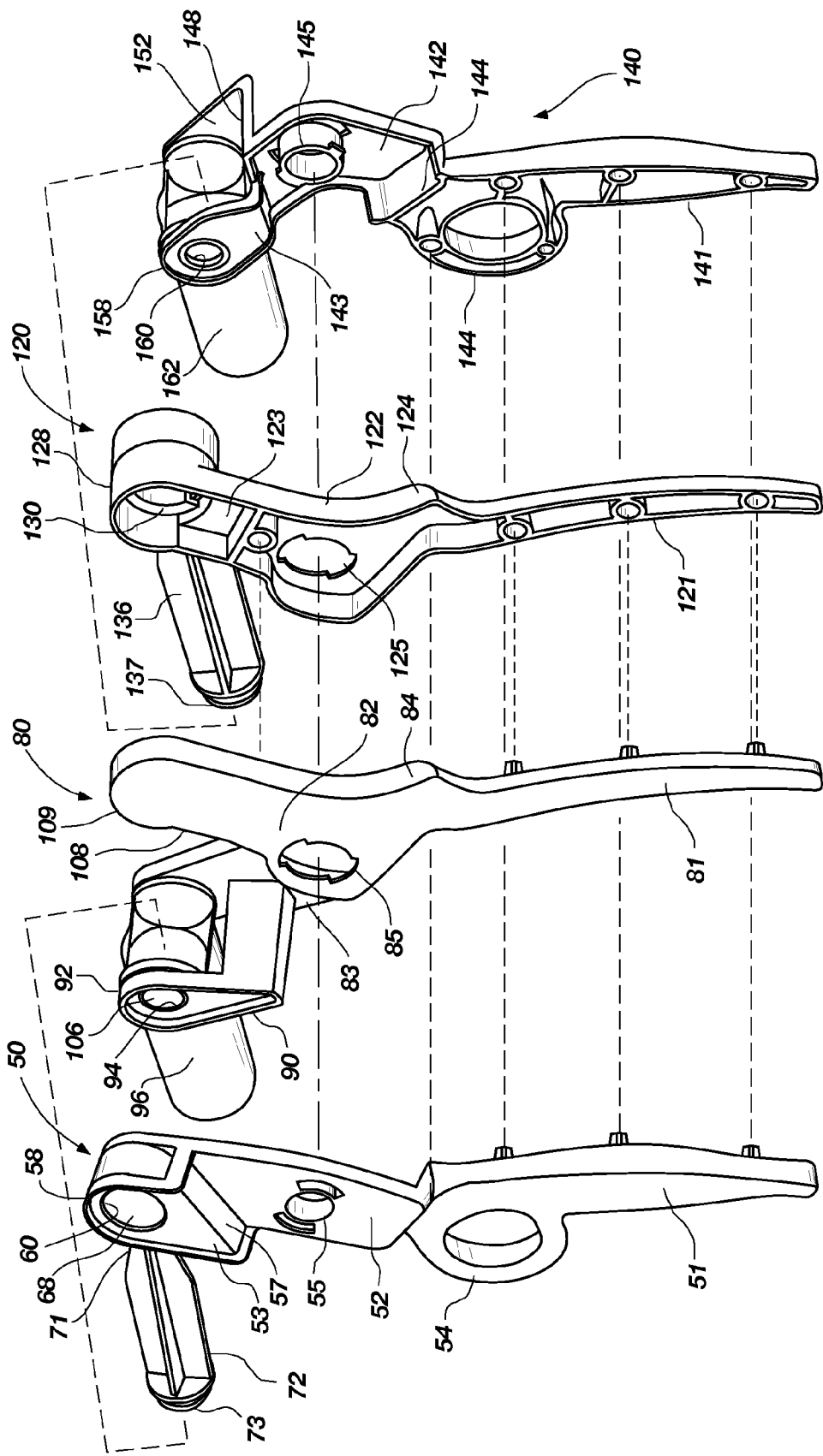
FIG. 3 is a rear perspective assembly view of the embodiment of syringe shown in FIGS. 1 and 2.
Figure 4:
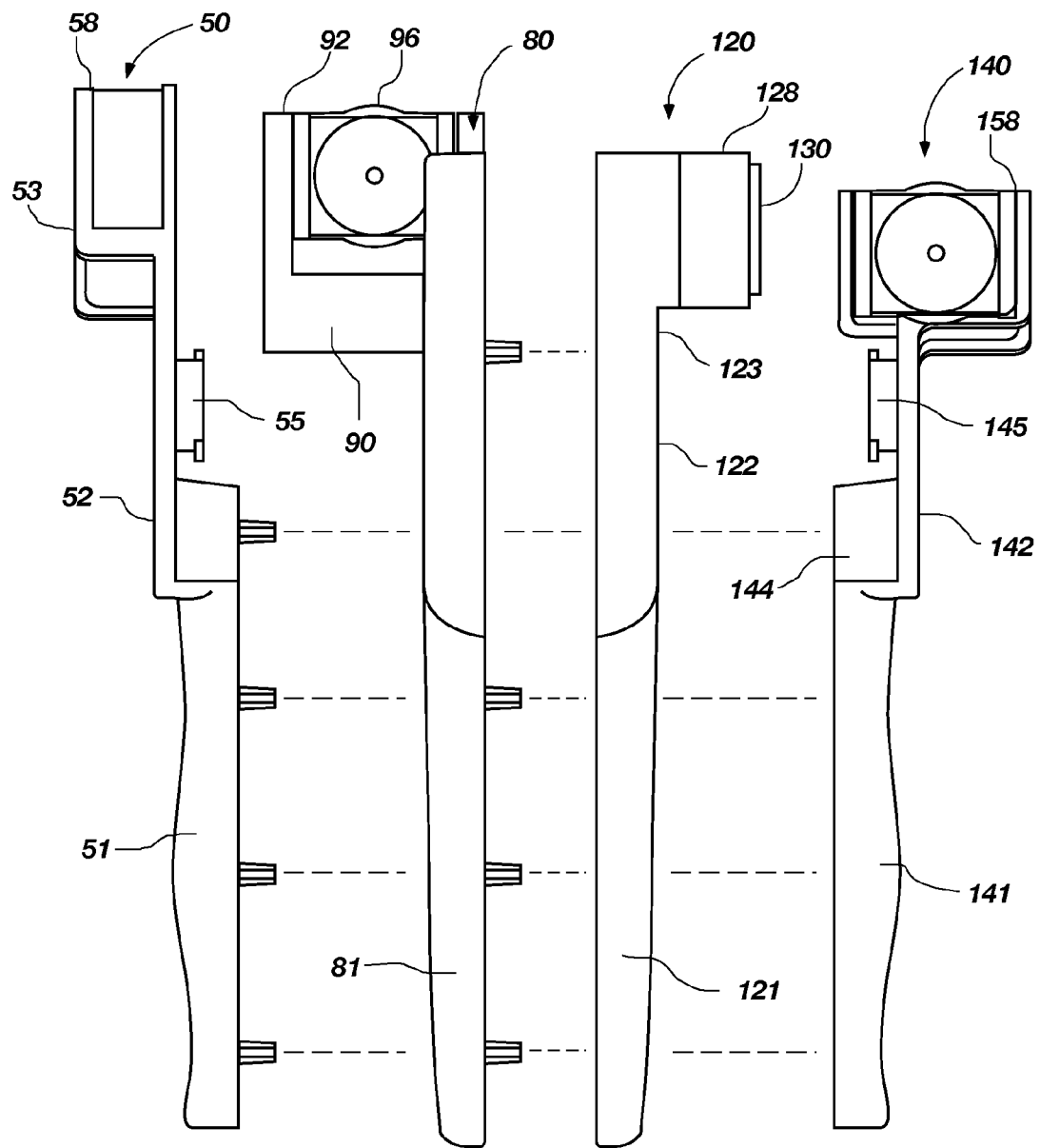
FIG. 4 is a rear plan assembly view of the embodiment of syringe shown in FIGS. 1 through 3.
Figure 6:
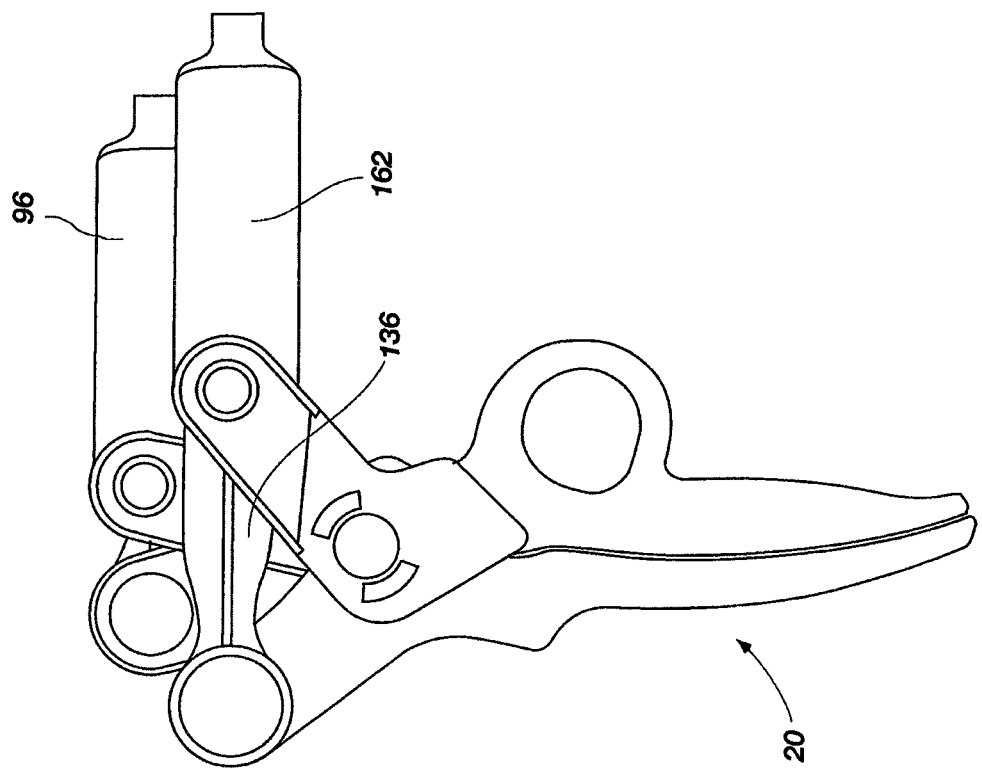
FIGS. 5 through 8 illustrate the embodiment of syringe shown in FIGS. 1 through 4 with the handles in a closed orientation.

In the embodiment shown in FIGS. 3 and 4, and with continued reference to FIGS. 1 and 2, the pair of handles 20 may be formed from four assembled pieces 50, 80, 120, and 140. The outer pieces 50 and 140 may be assembled to form front member 30 of the pair of handles 20, while the inner pieces 80 and 120 may be assembled to form rear member 40. In some embodiments, the outer pieces 50 and 140 may be rigidly secured to one another and/or the inner pieces 80 and 120 may be rigidly secured to one another.

The two left side pieces 50 and 80 of the pair of handles 20 shown in FIGS. 3 and 4 are configured to operate an infusion syringe 200. When proximal portions 31 and 41 of front member 30 and rear member 40, respectively, are squeezed or otherwise forced together, the two left-most pieces 50 and 80 of the pair of handles 20 are configured to force a plunger 72 (FIG. 7) distally into a receptacle 98 of the barrel 96 of an infusion syringe 200.

The two right side pieces 120 and 140 of the pair of handles 20 shown in FIGS. 1 and 2 are configured to operate an aspiration syringe 300 (best shown by FIG. 1). When proximal portions 31 and 41 of front member 30 and rear member 40 of handles 20 are squeezed or otherwise forced together, pieces 120 and 140 draw a plunger 136 (FIG. 11) of aspiration syringe 300 proximally out of a receptacle 164 of the barrel 162 of aspiration syringe 300.

The features of front and rear members 30 and 40, as well as their association with syringes 200 and 300 will now be described in further detail.

Figure 5:
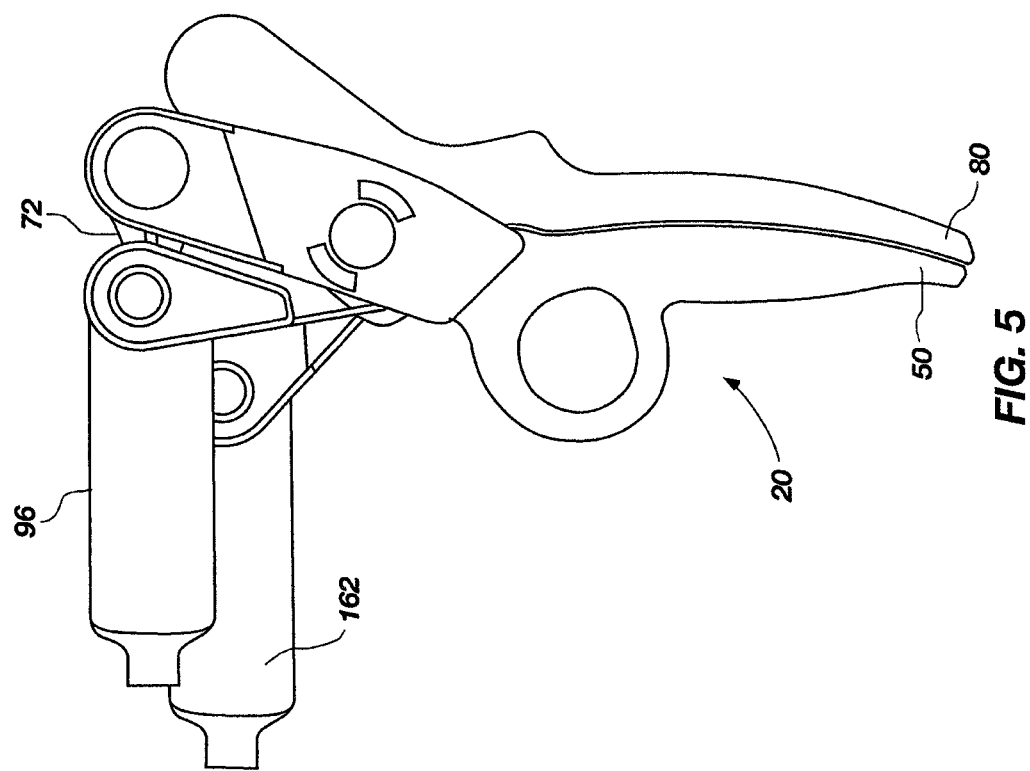
Figure 9:
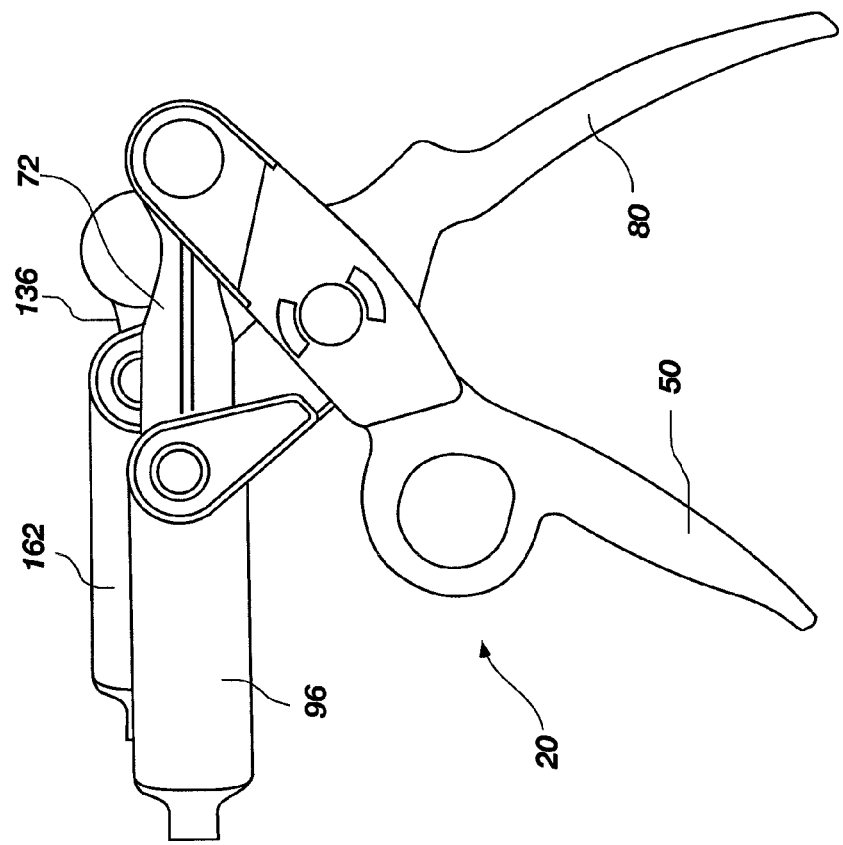

As FIG. 3 shows, the outer left piece 50 of handles 20, which forms half of front member 30 (as most clearly depicted by FIGS. 1 and 2), includes proximal portion 51, an intermediate portion 52, and a distal portion 53. When viewed from the side (see, e.g., FIGS. 5 and 9), piece 50 is slightly angled (e.g., at an angle of about 15° to about 30°) to facilitate grasping of handles 20 by a single hand, although it may be substantially straight. Proximal portion 51 of piece 50 is configured to be grasped by fingers of a user's hand, and may include a feature 54, such as a ring, that is configured to receive the user's index finger. Intermediate portion 52 of piece 50 includes features 55 that are configured to secure piece 50 to other pieces 80, 120, 140 of handles 20, such as the depicted aperture for receiving a pivot element of hinge 22 (FIG. 2). In the illustrated embodiment of piece 50, a line extending from a distal-most end of piece 50 to the most proximal end of piece 50 will intersect or come in close proximity to (e.g., within about a centimeter of) a pivot axis of hinge 22. Distal portion 53 of piece 50 may be pivotally secured to a plunger 72 of infusion syringe 200 (FIG. 1).

Figure 8:
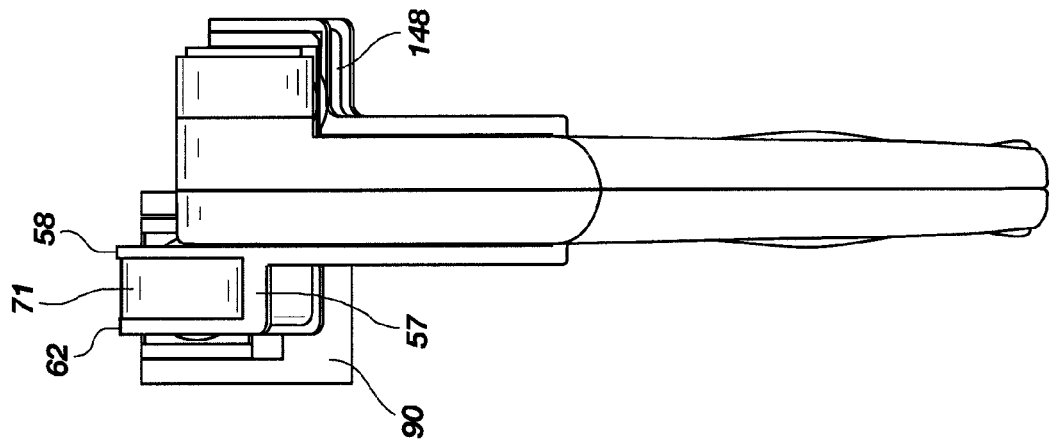
Figure 7:
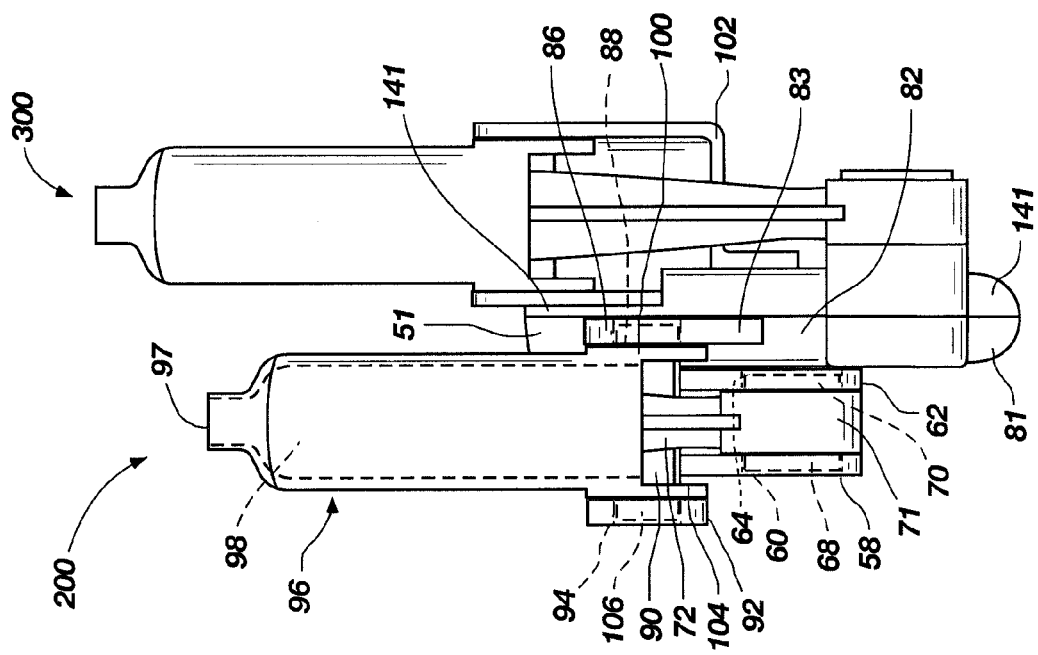
Figure 10:
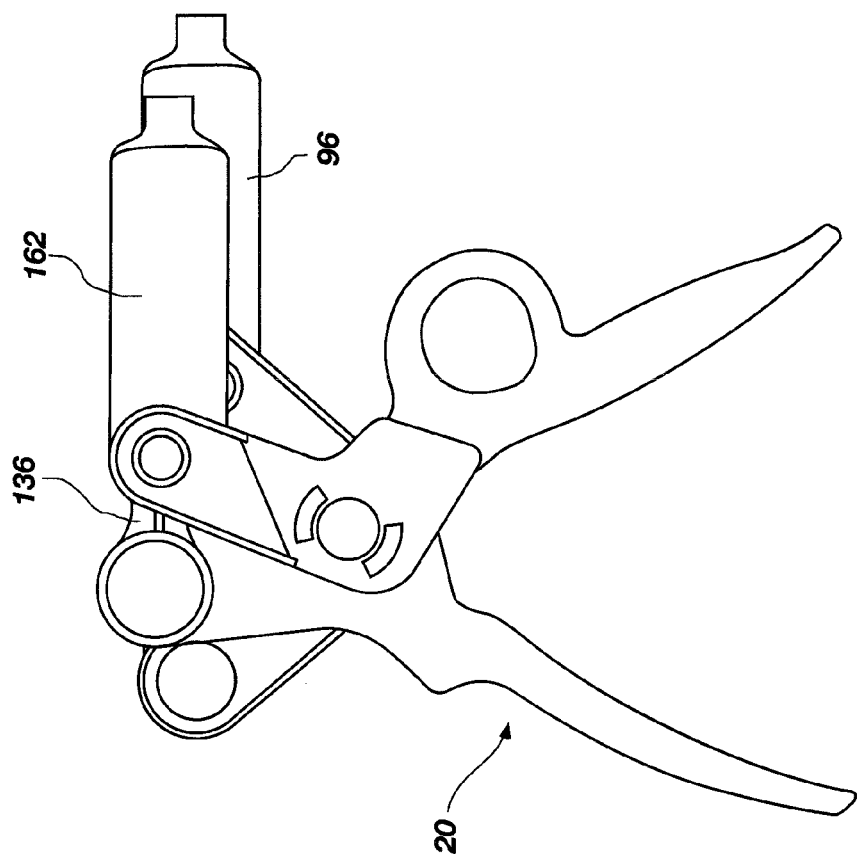

In this regard, as depicted in FIG. 7, along with continued reference to FIGS. 3 and 4, distal portion 53 may include a first arm 62 that pivotally engages one side of a proximal end 71 of plunger 72 and another arm 58 that pivotally engages another side of proximal end 71. In the depicted embodiment, arm 62 is merely the distal end of distal portion 53 of piece 50, while arm 58 protrudes upwardly, in substantially parallel relation to arm 62, from a ledge 57 extends laterally (to the left, when viewed from behind, as shown in FIGS. 8 and 12) from distal portion 53. Each arm 58, 62 includes a receptacle 60, 64 that engages and pivotally retains a pivot element 68, 70 protruding laterally from a proximal end 71 of plunger 72. As illustrated, pivot elements 68 and 70 may comprise circular protrusions with centers that are aligned with the centers of circular hinge receptacles 60 and 64, with all four aligned centers defining an axis about which distal portion 53 of piece 50 and proximal end 71 of plunger 72 pivot relative to one another.

With returned reference primarily to FIGS. 3 and 4, as well as to FIGS. 1 and 2, the inner left piece 80 of handles 20, which forms half of rear member 40 (best seen in FIG. 1), may be slightly angled (e.g., at an angle of about 15° to about 30°) to facilitate grasping of handles 20 by a single hand, although it may also be substantially straight. Like piece 50, piece 80 includes a proximal portion 81, an intermediate portion 82, and a distal portion 83. Proximal portion 81 is configured to be held by a thumb and palm of a user's hand. Piece 80 may also include a thumb retention feature 84, such as that appearing at a back edge of the illustrated embodiment. Intermediate portion 82 may include features 85, such as the depicted opening, that enable piece 80 to be pivotally secured to other pieces 50, 120, 140 of handles 20, such as with the pivot element of hinge 22 (best illustrated by FIG. 2). In the embodiment of piece 80 shown in FIG. 3, a line that extends from a distal-most end of piece 80 to the most proximal end of piece 80 will intersect or come in close proximity to (e.g., within about a centimeter of) a pivot axis of hinge 22 (see FIG. 2). Distal portion 83 of piece 80 may be pivotally secured to a proximal end of a barrel 96 of infusion syringe 200 (shown in FIG. 1).

An embodiment of the manner in which distal portion 83 of piece 80 may be pivotally secured to the proximal end of barrel 96 is shown in FIGS. 3 and 7. Distal portion 83 may include a pair of arms 86 and 92 that engage opposite sides of the proximal end of barrel 96 in a cradle-like arrangement. As illustrated, one arm 86 may merely comprise an extension of distal portion 83, while the other arm 92 protrudes from a ledge 90 that extends laterally (to the left, when viewed from behind, as shown in FIGS. 8 and 12) from distal portion 83. Arms 86 and 92 may include receptacles 88 and 94 that engage and pivotally retain pivot elements 102 and 106 that protrude from proximal extensions 100 and 104 on opposite sides of barrel 96. As depicted, pivot elements 102 and 106 may be circular in shape, or disk-shaped, so as to be received by, but rotate relative to, circular receptacles 88 and 94. Centers of receptacles 88 and 94 and of pivot elements 102 and 106 may be aligned to define an axis about which distal portion 83 of piece 80 and a proximal end of barrel 96 pivot relative to one another.

When piece 50 and piece 80 are assembled with one another, plunger 72 is disposed within a receptacle 98 of barrel 96.

With continued reference to FIG. 3, and to FIGS. 1 and 2, the inner right piece 120 of handles 20 is bent. Piece 120 includes a proximal portion 121, an intermediate portion 122, and a distal portion 123. Proximal portion 121 is configured to be held by the thumb and palm of the user's hand, and may include a thumb retention feature 124. Intermediate portion 122 includes an elbow that juts out from a front edge of piece 120. The elbow of intermediate portion 122 may include a feature 125, such as the depicted aperture, that is configured to secure piece 120 to other pieces 50, 80, 140 of handles 20. When feature 125 is an aperture, as depicted, it may be configured to receive a pivot element of hinge 22 (FIG. 2). In the illustrated embodiment of piece 120, feature 125 and a pivot axis through piece 120 are offset (e.g., by more than about one centimeter, by about two centimeters or more, etc.) from a line that extends from a distal-most end of piece 120 to the most proximal end of piece 120. Distal portion 123 of piece 120 may be pivotally secured to a plunger 136 of aspiration syringe 300 (FIG. 1).

Turning now to FIG. 11, and with additional reference to FIGS. 3 and 4, an end 128 of distal portion 123 of piece 120 includes a hub 130 that protrudes laterally (to the right in the embodiments shown in FIGS. 4 and 11) from end 128. Hub 130 defines an axis about which piece 120 pivots relative to plunger 136. Plunger 136 includes a receptacle 134 at its proximal end 132. Receptacle 134, which is configured to receive hub 130 and to rotate about hub 130, may have an annular appearance, with the remainder of plunger 136 extending distally therefrom.

Referring again to FIG. 3, as well as to FIGS. 1 and 2, the outer right piece 140 of handles 20 is bent. Piece 140 includes a proximal portion 141, an intermediate portion 142, and a distal portion 143. Proximal portion 141 is configured to be grasped by the fingers of a user's hand, and may include a feature 144, such as a ring, that is configured to receive the user's index finger. Intermediate portion 142 may have an L-shape, and includes an elbow that juts out from a back edge of piece 140. Intermediate portion 142 may also include a feature 145, such as the depicted pivot element of hinge 22 (FIG. 2), that is configured to define an axis about which front member 30 and rear member 40 of handles pivot relative to one another. Feature 145 may secure piece 140 to other pieces 50, 80, 120 of handles 20. In the illustrated embodiment of piece 140, due to the shape of intermediate portion 142, a pivot axis through feature 145 may be offset (e.g., by more than about one centimeter, by about two centimeters or more, etc.) from a line that extends from a distal-most end of piece 140 to the most proximal end of piece 140. Distal portion 143 of piece 140 may be pivotally secured to a barrel 162 of aspiration syringe 300 (FIG. 1).

As shown in FIGS. 3 and 11, a proximal end of barrel 162 may be cradled between opposed, distally protruding arms 152 and 158 of distal portion 143 of piece 140. More specifically, circular apertures 154 and 160 that extend through, or similar features (e.g., circular recesses in opposed surfaces of), arms 152 and 158 may receive and retain disk-shaped protrusions 168 and 172 on oppositely facing surfaces of proximal extensions 166 and 170 that are located on opposite sides of barrel 162. As illustrated, arm 158 may comprise an extension of distal portion 143, while arm 152 protrudes from a ledge 148 that extends laterally (to the right, as depicted in FIGS. 4, 8, and 12) from distal portion 143.

When piece 120 and piece 140 are assembled with each other, plunger 136 is disposed within a receptacle 164 of barrel 162.

Again returning reference to FIG. 3, the inner left piece 80 may include an extension 108 that protrudes from a rear edge of intermediate portion 82. Extension 108 may include a somewhat circular shaped distal end 109. When pieces 80 and 120 are assembled with each other and secured to one another, distal end 109 of extension 108 is axially aligned with distal end 128 of piece 120. This arrangement is configured to support distal end 128 when syringe 10 (see FIG. 1) is used.

With returned reference to FIGS. 1 and 2, when all of the pieces 50, 80, 120, and 140 of handles 20 are assembled with each other, pivotally connected front and rear members 30 and 40 are formed. The pivotal connection of front and rear members 30 and 40 enables proximal portions 31 and 41 of front and rear members 30 and 40, respectively, to be moved toward and away from another.

With added reference to FIG. 3, the features of front member 30 (which, in the depicted embodiment, is formed by the outer pieces 50 and 140) form a yoke 32. More specifically, a proximal end of the intermediate portion 52 of outer left piece 50 of handles 20 forms a first arm 34 of yoke 32 at an intermediate portion 35 of front member 30, while a proximal end of the intermediate portion 142 of piece 140 of handles 20 forms a second arm 36 of yoke 32 at intermediate portion 35 of front member 30. As illustrated, first arm 34 and second arm 36 of yoke 32 may be spaced apart from one another. At its distal end (and, thus, at a distal portion of the front member 30), the first arm 34 (on the left side of syringe 10 in the illustrated embodiment) of yoke 32 may be pivotally connected to the proximal end of plunger 72 of infusion syringe 200. A distal end of the second arm 36 (on the right side of syringe 10, at a distal end of the front member 30 in the illustrated embodiment) of yoke 32 may be pivotally connected to the proximal end of barrel 162 of aspiration syringe 300.

The features of rear member 40 (which, in the depicted embodiment, is formed by inner pieces 80 and 120) also form two arms 44 and 46. Arms 44 and 46 extend though yoke 32, between arms 34 and 36. A first arm 44 (on the left side of syringe 10 in the illustrated embodiment) may be pivotally connected to the proximal end of barrel 96 of infusion syringe 200. A second arm 46 (on the right side of syringe 10 in the illustrated embodiment) may be pivotally connected to the proximal end of plunger 136 of aspiration syringe 300.

The pivotal connections between the proximal ends of plungers 72 and 136, barrels 96 and 162 and their corresponding members 30 and 40 of handles 20 may be arranged such that the axes about which pivoting occurs are perpendicular to and intersect central axes extending along the lengths of plungers 72 and 136 and barrels 96 and 162.

In use, handles 20 of a syringe 10 that incorporates teachings of the present invention may be moved from an open position, where proximal portions 31 and 41 of front and rear members 30 and 40, respectively, are positioned apart from one another (i.e., have been moved away from one another), to a closed orientation, where proximal portions 31 and 41 are brought in close proximity to each other (i.e., have been moved toward one another). When handles 20 are in a fully open orientation, as shown in FIGS. 9 through 12, a distal end 73 of plunger 72 of infusion syringe 200 is located at a proximal end of receptacle 98 of barrel 96, while plunger 136 is completely inserted into a receptacle 164 of barrel 162 of aspiration syringe 300, with a distal end 137 of plunger 136 located at a distal end of receptacle 164. As handles 20 are moved toward the closed orientation (see, e.g., FIGS. 1 and 2, which show handles 20 in an intermediate orientation), plunger 72 moves distally into receptacle 98 of barrel 96, while plunger 136 is withdrawn proximally through receptacle 164 of barrel 162. Plungers 72 and 136 may be continuously moved through substantially the entire lengths of the receptacles 98 and 164 of their corresponding barrels 96 and 162 with a single squeeze of handles 20. When handles 20 are in a fully closed orientation, as shown in FIGS. 5 through 8, plunger 72 is completely inserted into receptacle 98 of barrel 96, with distal end 73 of plunger 72 being located at a distal end of receptacle 98, while distal end 137 of plunger 136 is located at a proximal end of receptacle 164 of barrel 162.

Due to the configuration of handles 20 in the illustrated embodiment, when handles 20 are actuated, infusion syringe 200 and aspiration syringe 300 may move somewhat in opposite directions.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A syringe, comprising:
   a first syringe, including a first barrel and a first plunger;
   a second syringe, including a second barrel and a second plunger; and
   handles, including:
      a first member, including:
         a first piece pivotally connected to a proximal end of the first plunger; and
         a second piece pivotally connected to the second barrel; and
      a second member, including:
         a first piece pivotally connected to the first barrel; and
         a second piece pivotally connected to a proximal end of the second plunger,
      the handles configured to force the first plunger a first direction through the first barrel while forcing the second plunger a second direction, opposite from the first direction, through the second barrel.

2. The syringe of claim 1, wherein the first barrel and the second barrel include distal ends pointing in substantially the same direction.

3. The syringe of claim 1, wherein the first member and the second member of the handles are pivotally connected to one another.

4. The syringe of claim 1, wherein:
   the first and second pieces of the first member of the handles are rigidly secured to one another; and
   the first and second pieces of the second member of the handles are rigidly secured to one another.

5. The syringe of claim 1, wherein a distal end of the first member of the handles forms a yoke for receiving a distal end of the second member of the handles.

6. The syringe of claim 1, wherein the first and second members of the handles have an open orientation, in which the first and second members are spaced as far as possible apart from each other, and a closed orientation, in which the first and second members are positioned as close as possible to one another.

7. The syringe of claim 6, wherein:
   with the handles in the open orientation:
      a distal end of the first plunger is positioned at a proximal end of the first barrel; and
      a distal end of the second plunger is located at or adjacent to a distal end of the second barrel; and
   with the handles in the closed orientation:
      the distal end of the first plunger is located at or adjacent to the distal end of the first barrel; and
      the distal end of the second plunger is positioned at a proximal end of the second barrel.

8. A syringe, comprising:
   a first syringe, including a first barrel and a first plunger;
   a second syringe, including a second barrel and a second plunger; and
   handles configured to force the first plunger a first direction through the first barrel while drawing the second plunger a second direction through the second barrel, the handles including:
      a first member pivotally connected to:
         a proximal end of the first plunger; and
         the second barrel; and
      a second member pivotally connected to:
         the first barrel; and
         a proximal end of the second plunger,
      a first member and the second member being pivotally connected to one another.

9. The syringe of claim 8, wherein the handles are configured to force the first plunger the first direction through the first barrel while forcing the second plunger the second direction through the second barrel as the first member and the second member of the handles move toward one another.

10. The syringe of claim 8, wherein the handles are configured to move the first barrel and the second barrel relative to one another as relative positions of the first member and the second member change.

11. A syringe, comprising:
    a first syringe, including a first barrel and a first plunger;
    a second syringe, including a second barrel and a second plunger; and
    handles, including:
       a first member pivotally connected to a proximal end of the first plunger and to the second barrel; and
       a second member pivotally connected to the first barrel and to a proximal end of the second plunger,
       the first member and the second member being pivotally connected to one another, the handles configured to force the first plunger a first direction through the first barrel while forcing the second plunger a second direction, opposite from the first direction, through the second barrel.

12. The syringe of claim 11, wherein the first barrel and the second barrel include distal ends pointing in substantially the same direction.

13. The syringe of claim 11, wherein the first and second members of the handles have an open orientation, in which the first and second members are spaced as far as possible apart from each other, and a closed orientation, in which the first and second members are positioned as close as possible to one another.

14. The syringe of claim 13, wherein:
    with the handles in the open orientation:
       a distal end of the first plunger is positioned at a proximal end of the first barrel; and
       a distal end of the second plunger is located at or adjacent to a distal end of the second barrel; and
    with the handles in the closed orientation:
       the distal end of the first plunger is located at or adjacent to the distal end of the first barrel; and
       the distal end of the second plunger is positioned at a proximal end of the second barrel.

* * * * *